United States Patent
Siemons et al.

(10) Patent No.: US 11,089,971 B2
(45) Date of Patent: Aug. 17, 2021

(54) THERMODILUTION INJECTATE MEASUREMENT AND CONTROL

(71) Applicant: EDWARDS LIFESCIENCES CORPORATION, Irvine, CA (US)

(72) Inventors: Alexander H. Siemons, Yorba Linda, CA (US); Wei-Jiun Liu, Newport Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 15/321,685

(22) PCT Filed: Oct. 21, 2015

(86) PCT No.: PCT/US2015/056765
§ 371 (c)(1),
(2) Date: Dec. 22, 2016

(87) PCT Pub. No.: WO2017/069755
PCT Pub. Date: Apr. 27, 2017

(65) Prior Publication Data
US 2017/0265756 A1    Sep. 21, 2017

(51) Int. Cl.
*A61B 5/028* (2006.01)
*A61B 5/00* (2006.01)
(Continued)

(52) U.S. Cl.
CPC .............. *A61B 5/028* (2013.01); *A61B 5/029* (2013.01); *A61B 5/0295* (2013.01);
(Continued)

(58) Field of Classification Search
CPC .................................................... A61B 5/028
See application file for complete search history.

(56) References Cited

U.S. PATENT DOCUMENTS 4,024,864 A * 5/1977 Davies .................. A61B 6/481
604/67
5,526,817 A  6/1996 Pfeiffer et al.
(Continued)

FOREIGN PATENT DOCUMENTS

EP    1034737 A1   9/2000
JP    02026532     1/1990
(Continued)

OTHER PUBLICATIONS

Int'l. Search Report for PCT/US2015/056765, dated Jul. 5, 2016.

*Primary Examiner* — Puya Agahi
(74) *Attorney, Agent, or Firm* — Chang & Hale; Fred T. Hale; Alan T. Hale

(57) ABSTRACT

Apparatus and methods for the measurement, control, or both, of thermodilution injectate flow for calculation of transpulmonary thermodilution parameters. An injectate delivery system includes a syringe for holding an injectate and a conduit configured at one end to be connected to a catheter. A flow measurement device is interposed in the conduit to generate a signal for determining the flow rate of the fluid from the syringe to the catheter. A processor receives the signal from the flow measurement device and calculates the injectate volume to be used as input for calculating a transpulmonary thermodilution parameter such as cardiac output. A GUI is provided to direct a user on whether the injection rate is too fast or too slow. Rather than measuring or calculating flow rate, a system may include a constant flow valve to provide a constant flow rate from the syringe.

19 Claims, 8 Drawing Sheets

(51) Int. Cl.
*A61B 5/029* (2006.01)
*A61B 5/0295* (2006.01)

(52) U.S. Cl.
CPC .......... *A61B 5/6852* (2013.01); *A61B 5/7285* (2013.01); *A61B 5/742* (2013.01); *A61B 5/7275* (2013.01)

(56) References Cited

U.S. PATENT DOCUMENTS

| | | |
|---|---|---|
| 5,676,145 A | 10/1997 | Bar-Lavie |
| 6,061,590 A | 5/2000 | Krivitski |
| 6,986,744 B1 | 1/2006 | Krivitski |
| 2002/0156464 A1* | 10/2002 | Blischak ............ A61M 5/14276 604/892.1 |
| 2003/0033095 A1 | 2/2003 | Svanerudh et al. |
| 2003/0158490 A1 | 8/2003 | Krivitski et al. |
| 2005/0107697 A1 | 5/2005 | Berke |
| 2006/0211947 A1* | 9/2006 | Krivitski ............ A61B 5/0275 600/504 |
| 2007/0060820 A1* | 3/2007 | Lofgren ............... A61B 5/0215 600/481 |
| 2007/0088216 A1 | 4/2007 | Pfeiffer et al. |
| 2011/0208072 A1 | 8/2011 | Pfeiffer et al. |
| 2012/0271168 A1* | 10/2012 | Radojicic ............ A61M 5/1723 600/439 |
| 2013/0317359 A1 | 11/2013 | Wilson et al. |
| 2014/0081157 A1* | 3/2014 | Joeken ................... A61B 5/028 600/484 |
| 2014/0128733 A1 | 5/2014 | Eggers et al. |
| 2015/0065956 A1 | 3/2015 | Huang et al. |
| 2015/0283342 A1* | 10/2015 | Mielcarz ............ G09B 23/288 128/202.22 |

FOREIGN PATENT DOCUMENTS

| | | | |
|---|---|---|---|
| JP | 11318834 | 3/1999 | |
| WO | 92015256 A1 | 9/1992 | |
| WO | 2009049252 A1 | 4/2009 | |
| WO | 2011096421 A1 | 8/2011 | |
| WO | 2012071307 A2 | 5/2012 | |
| WO | WO 2014120842 A1 * | 8/2014 | ............... A61B 5/08 |

* cited by examiner

THERMODILUTION INJECTATE MEASUREMENT AND CONTROL

FIELD

Aspects of the disclosure generally relate to apparatus and methods for measurement, control, or both, of fluid discharged from a syringe or other reservoir, and in particular may relate to accuracy of measured or calculated transpulmonary thermodilution parameters.

BACKGROUND

Thermodilution is the most widely used technique for determining cardiac output. The thermodilution method applies indicator dilution principles, using temperature change as the indicator.

A known amount of solution with a known temperature is injected rapidly into the right atrial lumen of a first catheter. This cooler solution mixes with and cools the surrounding blood, and the temperature is measured downstream in the pulmonary artery by a thermistor bead embedded in a second catheter. The resultant change in temperature is then plotted on a time-temperature curve. This curve is similar to the one produced by the indicator-dilution method.

A normal curve characteristically shows a sharp upstroke from rapid injection of the injectate. This is followed by a smooth curve and slightly prolonged downslope back to the baseline. Since this curve is representing a change from warmer temperature to cooler and then back to warmer temperature, the actual curve is in a negative direction. In many illustrative and display graphs, the curve is produced in an upright fashion, so that the area under the curve is inversely proportional to the cardiac output.

When cardiac output is low, more time is required for the temperature to return to baseline, producing a larger area under the curve. With high cardiac output, the cooler injectate is carried faster through the heart, and the temperature returns to baseline faster. This produces a smaller area under the curve.

Critical to the technique is the injectate temperature, volume, and flow rate. As the result of rates of injections differing between users who perform the procedure, however, actual volume and solution temperature of the injectate, or injected cold bolus, may vary considerably, with a loss of accuracy and precision of the cardiac output measurement. Some users apply extreme force to the syringe to inject the bolus as quickly as possible, while others inject at a slower rate. Mistakes may be made by the user when injecting the bolus, including injecting a different volume than the quantity that was entered into a monitoring device and on which calculations are based.

SUMMARY

In accordance with one embodiment of the concepts disclosed herein, an injectate delivery system is provided. The system includes a reservoir for holding a fluid injectate, a conduit in fluid communication with the reservoir and configured at one end to be connected to a catheter, and a manually or mechanically driven syringe, another form of injector, or other means for manually discharging the fluid from the reservoir to the conduit. A flow measurement device is interposed in the conduit, and the flow measurement device is configured for generating a signal used in determining the flow rate of the fluid from the reservoir to the catheter. A processing device is adapted to receive the signal from the flow measurement device and is configured to calculate injectate volume to be used as input for calculating at least one parameter. In some embodiments, the at least one parameter to be calculated is a transpulmonary thermodilution parameter, and in some such embodiments, the transpulmonary thermodilution parameter is at least one of cardiac output, global end diastolic volume, and extra vascular lung water.

In some embodiments and in combination with any of the above embodiments, the reservoir is a syringe, and the means for manually discharging the fluid is a plunger of the syringe. In some such embodiments, the system further comprises a catheter in fluid communication with the reservoir, and in some of these embodiments, the catheter is a Swan-Ganz® catheter, manufactured and sold by Edwards Lifesciences.

In some embodiments and in combination with any of the above embodiments, the flow measurement device is configured to generate the signal to the processing device based on differential pressure. In some embodiments and in combination with any of the above embodiments, the flow measurement device comprises pressure sensors for measuring a pressure drop across an orifice. In some embodiments and in combination with any of the above embodiments, the flow measurement device defines an area of constricted flow and comprises pressure sensors for measuring vortex differential pressure. In some embodiments and in combination with any of the above embodiments, the flow measurement device comprises a Venturi tube. In some embodiments and in combination with any of the above embodiments, the flow measurement device comprises pitot tubes. In some embodiments and in combination with any of the above embodiments, the flow measurement device comprises a hot wire anemometer.

In some embodiments and in combination with any of the above embodiments, a sensor interposed in the conduit is configured to detect changes in pressure or temperature of the injectate and to signal a timer to start at the beginning of the injection and stop at the end of the injection to measure elapsed time of an injection.

In accordance with another embodiment of the concepts disclosed herein, a method for determining injectate volume for use in the determining transpulmonary thermodilution parameters is provided. The method includes starting, by a processor, a timer upon receiving a signal of an increase in pressure at a pressure sensor indicating the start of an injection of a fluid injectate into a conduit from a syringe. A signal is received by a processor from a flow measurement device interposed in the conduit. A processor calculates a flow rate of the injectate. The timer is stopped to determine the elapsed time of the injection, and a processor calculates a volume of injectate that has been injected. The calculated volume is used in calculating at least one transpulmonary thermodilution parameter.

In some embodiments and in combination with the above embodiment, the transpulmonary thermodilution parameter is at least one of cardiac output, global end diastolic volume, and extra vascular lung water. In some embodiments and in combination with any of the above embodiments, the method further comprises graphically displaying a current flow rate of injectate. In some such embodiments, the method further comprises graphically displaying a predetermined minimum flow rate and a predetermined maximum flow rate that define limits within which the current flow rate is desired to appear.

In accordance with another embodiment of the concepts disclosed herein, an injectate delivery system is provided.

The injectate delivery system includes a reservoir for holding a fluid injectate, a conduit in fluid communication with the reservoir and configured at one end to be connected to a catheter, and a syringe, an injector, or another means for manually discharging the fluid injectate from the reservoir to the conduit during an injection. A constant flow control element is fluidically interposed in the conduit, and the constant flow control element is configured to maintain a substantially constant design flow rate for the duration of the injection for the flow of the fluid from the reservoir to the catheter. A sensor is interposed in the conduit configured to detect changes in pressure or temperature of the injectate and to signal a timer to start at the beginning of the injection and stop at the end of the injection. A processing device is adapted to receive a signal from a sensor, with the processing device being configured to calculate injectate volume based on the constant flow valve design flow rate and measured elapsed time of the injection. The volume is to be used as input for calculating at least one parameter. In some such embodiments, the at least one parameter to be calculated is a transpulmonary thermodilution parameter including at least one of cardiac output, global end diastolic volume, and extra vascular lung water.

In some embodiments and in combination with any of the above embodiments, the reservoir comprises a syringe and the constant flow control element comprises a constant flow valve fluidically interposed in the conduit. In other embodiments and in combination with any of the above embodiments, the reservoir comprises a syringe and the syringe comprises the constant flow control element as an integral feature of the syringe.

In accordance with another embodiment of the concepts disclosed herein, a method of displaying a relative flow rate for an injectate delivery system is provided. The method includes calculating, by a processor, a flow rate of a fluid injected into a conduit for a thermodilution procedure using parameters measured by a flow measurement device. The processor graphically displays on a display device an indication of a predetermined minimum acceptable flow rate, a predetermined maximum acceptable flow rate, and the current flow rate relative to the minimum and maximum acceptable flow rates.

In accordance with another embodiment of the concepts disclosed herein, a system for displaying a relative flow rate for an injectate delivery system is provided. The system includes a display device, a processor operably connected to the display device; and a memory. The memory is operably connected with the processor to store a predetermined minimum acceptable flow rate and a predetermined maximum acceptable flow rate, and is also operably connected to store computer program code which, when executed, causes the processor to calculate a flow rate of a fluid injected into a conduit for a thermodilution procedure using parameters measured by a flow measurement device, and graphically present, on the display device, an indication of the predetermined minimum acceptable flow rate, the predetermined maximum acceptable flow rate, and the current flow rate relative to the minimum and maximum acceptable flow rates.

In accordance with another embodiment of the concepts disclosed herein, an apparatus for displaying a relative flow rate for an injectate delivery system is provided. The apparatus includes means for storing a predetermined minimum acceptable flow rate and a predetermined maximum acceptable flow rate, means for calculating a flow rate of a fluid injected into a conduit for a thermodilution procedure using parameters measured by a flow measurement device, and means for graphically displaying an indication of the predetermined minimum acceptable flow rate, the predetermined maximum acceptable flow rate, and the current flow rate relative to the minimum and maximum acceptable flow rates.

BRIEF DESCRIPTION OF THE DRAWINGS

For a more complete understanding, reference should now be had to the embodiments shown in the accompanying drawings and described below. In the drawings.

DETAILED DESCRIPTION

Figure 1:
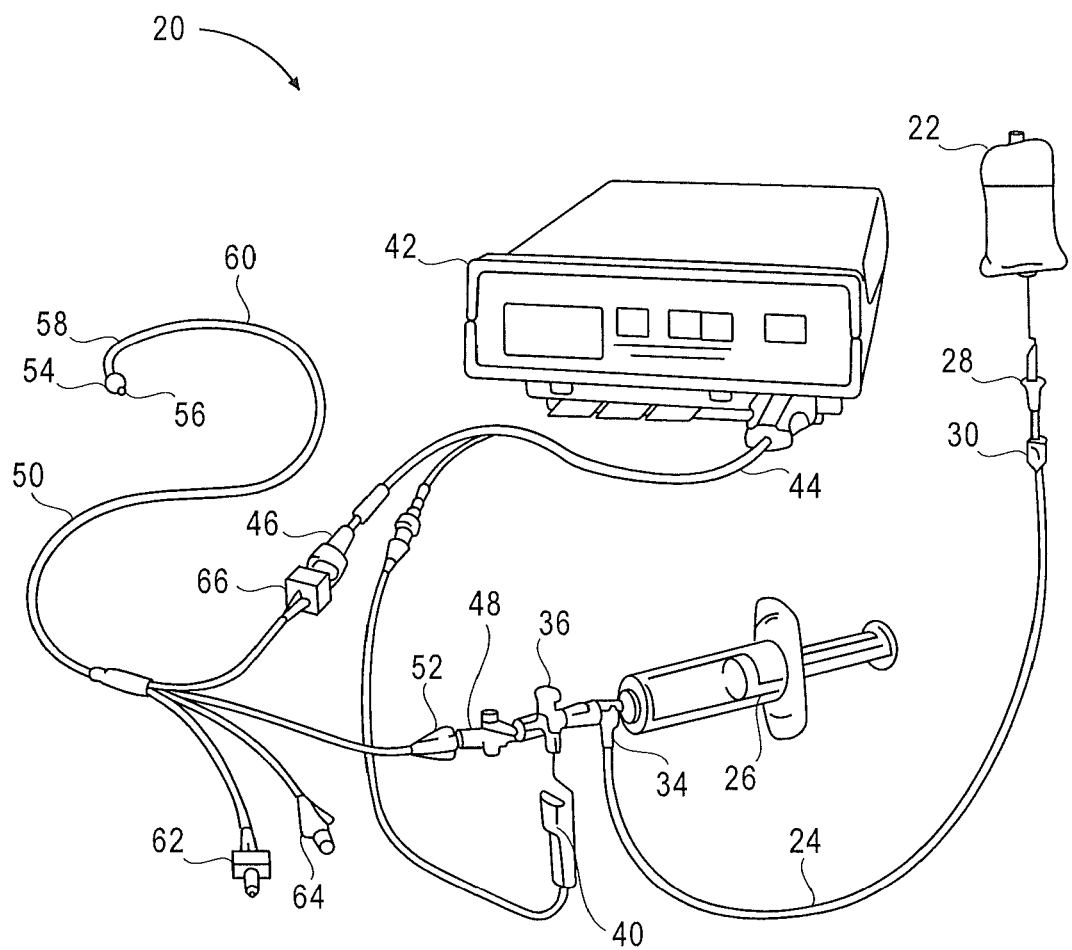
FIG. 1 is a perspective view of a prior art injectate delivery system.

The following detailed description of embodiments refers to the accompanying drawings, which illustrate specific embodiments. Other embodiments having different structures and operation do not depart from the scope of the present disclosure.

Embodiments of concepts disclosed herein are directed to apparatus and methods for measuring, controlling, or both, characteristics of an injected bolus. The characteristics may include, for example, pressure, temperature, and flow, and although the disclosed apparatus and methods may apply to automated devices such a syringe pumps, they are discussed herein with respect to manually operated syringes and reservoirs. In addition, real-time feedback may be provided to a user to help reduce variability in the injection technique as well as reduce the potential for user error in entering data into the monitoring device.

As will be appreciated by one of skill in the art, the present invention may be embodied as a method, device, article, system, computer program product, or a combination of the foregoing. Any suitable computer usable or computer readable medium may be utilized for a computer program product including non-transitory computer program code to implement all or part of an embodiment of the invention. The computer usable or computer readable medium may be, for example but not limited to, a tangible electronic, magnetic, optical, electromagnetic, or semiconductor system, apparatus or device.

There are two primary injectate delivery systems for thermodilution procedures. One is an open system that utilizes prefilled syringes, with injectate either iced or at room temperature. The other is a closed system, also either for iced or room temperature injectate, which is maintained in a closed-loop fashion to reduce multiple entries into a sterile system. Available data suggest that there will be less variability in cardiac output determinations if iced solution is used. Optionally, an injectate temperature that is warmer than body temperature could be used. A computer registers a change in temperature, which may be through a signal, from the patient's baseline, which may be noise. In some conditions, a variation in temperature of 0.05° C. may occur with respirations. This decreases the "signal-to-noise" ratio and may produce an abnormally low cardiac output value. Other conditions where an increased signal-to-noise ratio may be beneficial include febrile patients, low cardiac output states, and patients with wide respiratory variations.

A modified Stewart-Hamilton equation is used to calculate the cardiac output, taking into consideration the change in temperature as the indicator. Modifications include the measured temperature of the injectate and the patient's blood temperature, along with the specific gravity of the solution injected. The Stewart-Hamilton equation is as follows:

$$CO=(V \times (T_B-T_I)/A) \times (S_I \times C_I)/(S_B \times C_B) \times (60 \times C \times K)$$

Where:
CO=cardiac output
V=Volume of injectate (mL)
A=area of thermodilution curve in square mm divided by paper speed (mm/sec)
$T_B$, $T_I$=temperature of blood (B) and injectate (I)
$S_B$, $S_I$=specific gravity of blood and injectate
$C_B$, $C_I$=specific heat of blood and injectate
$(S_I \times C_I)/(S_B \times C_B)$=1.08 when 5% dextrose is used
60=60 sec/min
$C_T$=correction factor for injectate warming A dilution apparatus, method, and computer program applicable to thermodilution is disclosed in U.S. Pat. No. 8,343,058, to Pfeiffer et al., issued Jan. 1, 2013, and assigned to Edwards Lifesciences IPRM AG, the contents of which are hereby incorporated by reference in their entirety. At least three key transpulmonary thermodilution parameters may be impacted by injectate volume, being cardiac output, global end diastolic volume, and extra vascular lung water.

Referring to the drawings, where like reference numerals refer to the same or similar parts, FIG. 1 shows a prior art injectate delivery system 20, which in this embodiment is an open system. The system 20 includes a sterile injectate solution reservoir 22 connected with injectate delivery tubing 24 to an outlet or tubing connected to the outlet of a syringe 26. A non-vented IV spike 28 and a means of stopping flow from the tubing, such as a snap clamp 30, may be provided along the injectate delivery tubing 24. A check valve 34 may be provided proximate to the connection of the tubing 24 to the syringe outlet to allow flow from the reservoir 22 to the syringe 26, but not allow flow back to the reservoir 22.

Downstream of the connection of the check valve 34 to the syringe outlet, a flow-through housing 36 may be provided that receives a temperature probe 40. The temperature probe 40 is one of several features electrically connected to a computer 42, which may include an associated processor or processing device, CPU, monitor, and control unit, with electrical cables 44 and catheter connectors 46. A three-way stopcock and continuous flush device 48 may be connected downstream of the flow-through housing 36 for the temperature probe 40. The most downstream element may be a catheter 50, which may be, for example, a Swan-Ganz catheter. The catheter 50 may include a proximal injectate hub 52. At the distal end of the catheter 50 there may be a balloon 54 and a distal lumen 56, with a thermistor 58 proximate to the balloon 54 and spaced from a proximal injectate port 60. At the proximal end of the catheter 50, in addition to the proximal injectate hub 52 there may be a balloon inflation valve 62, an IV/pressure monitoring line 64, and a thermistor connector 66, connected with a catheter connector 46 to the computer 42.

Figure 2:
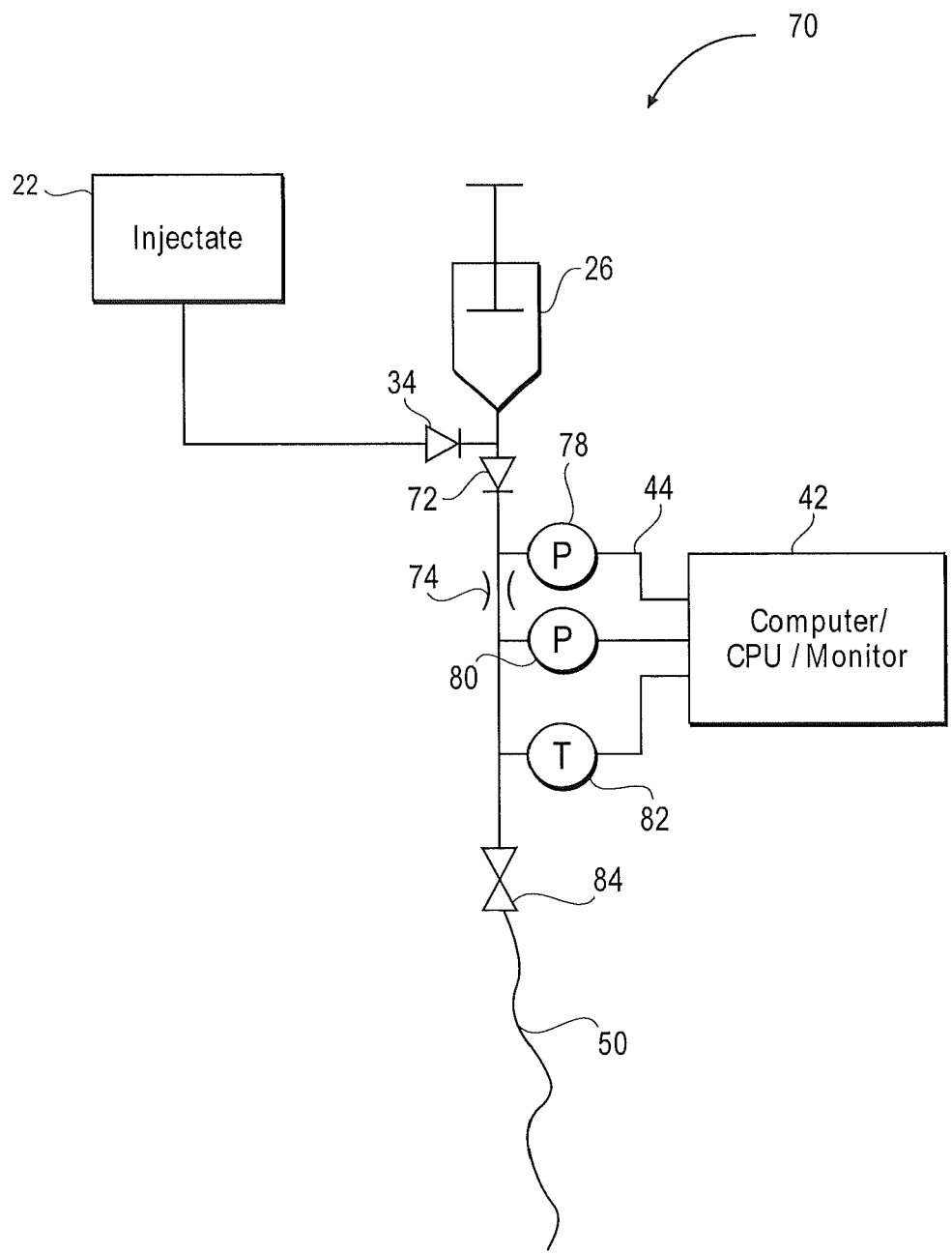
FIG. 2 is a schematic view of an injectate delivery system in accordance with example embodiments of the invention.

An example embodiment according to the invention of an injectate delivery system 70 is shown schematically in FIG. 2. In this embodiment, a flow measurement device may be provided. In the flow measurement device a pressure differential may measured across a pressure reducing feature, such as, for example, an orifice, a constricted flow area resulting in vortex differential pressure, a differential pressure transducer, or a Venturi tube, in order to calculate a flow rate of injectate. The flow measurement device may alternatively include pitot tubes or a hot wire anemometer-type device. Taken over a measured time, the flow rate may be used to calculate a volume of injectate, which in turn may be used in the Stewart-Hamilton equation and the equations of incorporated U.S. Pat. No. 8,343,058, and may provide a more accurate result than might otherwise be reached.

The injectate delivery system 70 of FIG. 2 may include a reservoir such as a syringe 26 that may draw from an injectate reservoir 22, with a check valve 34 allowing flow from the reservoir 22 but preventing flow back to the reservoir 22. Alternatively, the reservoir 22, tubing 24, and check valve 34 may be omitted, leaving the system closed, with only the syringe 26 as the source of injectate; the syringe 26 may be pre-filled and itself cooled. Another check valve 72 may be provided that allows the flow of discharged injectate from the syringe 26, but prevents backflow into the syringe 26 from tubing 24 when the syringe 26 is aspirated to draw injectate from the reservoir 22. A flow measurement device 74, as described above, may be inserted in line with the tubing 24. Pressure sensors 78, 80 may be provided upstream and downstream of the flow measurement device 74, and a temperature sensor 82, which may be a thermistor, may be provided as well, preferably downstream of the flow measurement device 74. The pressure sensors 78, 80 and temperature sensor 82 may be connected to the computer 42 with cables 44. A stopcock 84 or other valve may be provided and may be connected to a proximal injectate hub (not shown). The catheter 50 is represented by a single line in FIG. 2, but it should be understood that there may be multiple connection lines incorporated in the catheter that serve a variety of functions, as exemplified in FIG. 1.

The flow measurement device 74 may have known flow characteristics and flow area that provide a relationship between pressure loss and velocity of the injectate, such that when the pressure loss is known, the velocity may be determined. In addition, the initial change in pressure, or if desired, temperature, when the bolus discharge from the syringe 26 begins may trigger a timer to start in the computer 42. With the velocity and the fluid characteristics of the injectate known, and the elapsed time being measured, the volume of the injectate may be calculated.

Figure 3:
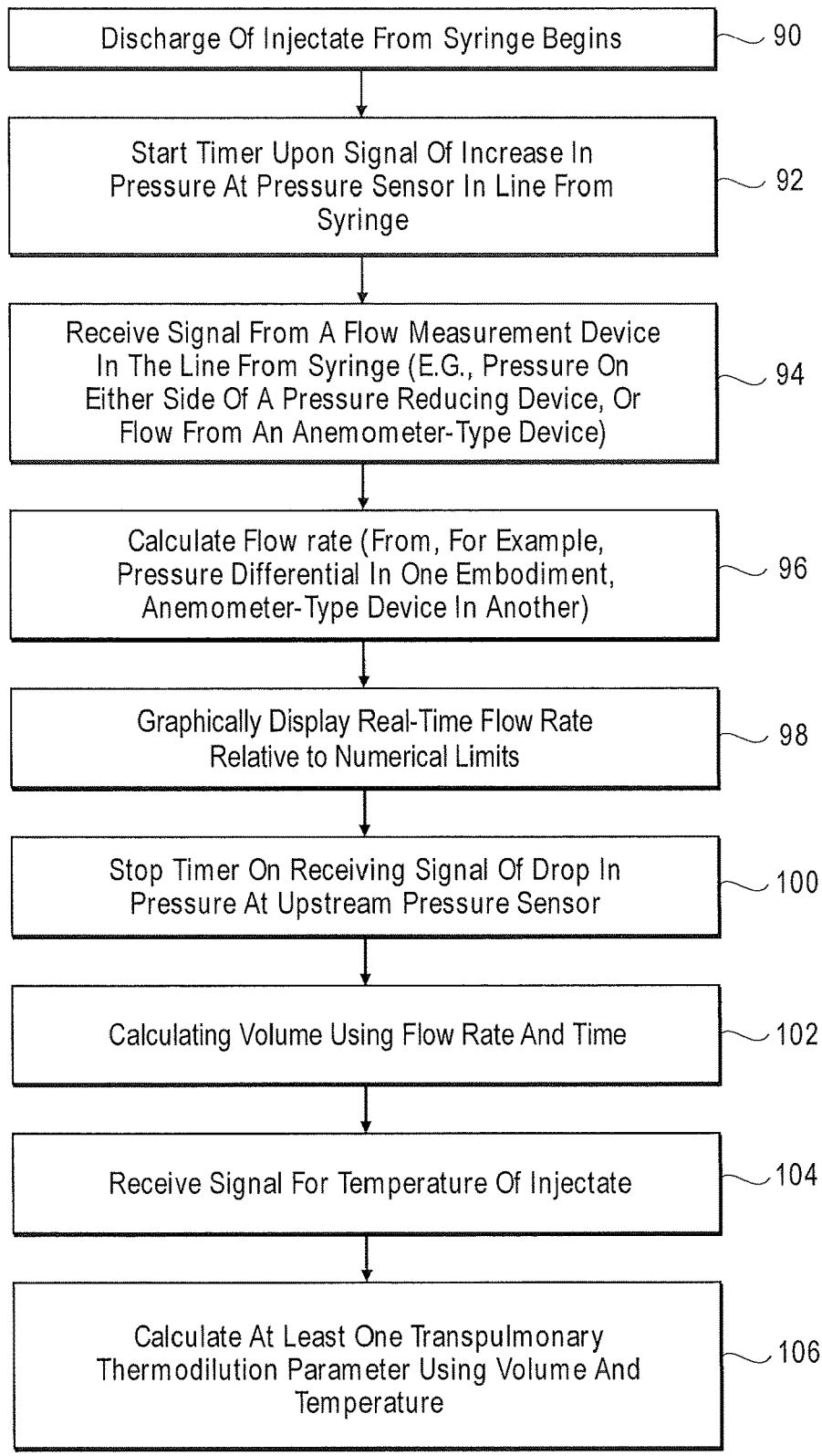
FIG. 3 is a flowchart illustrating a process that can be carried out with example embodiments of the invention.

An embodiment of a process 88 for determining injectate volume for use in the determining transpulmonary thermodilution parameters is shown in FIG. 3. First, discharge of injectate from a syringe begins 90. A timer starts upon receiving a signal of an increase in pressure at a pressure sensor 92, for example, at a pressure sensor in the line from the syringe; which pressure sensor to use, or both, may be selected as desired to suit the application and apparatus. A signal is received from a flow measurement device in the line from the syringe 94, which may be on both sides of a pressure reducing device (upstream and downstream), or alternatively from flow that cools a hot wire anemometer to generate a signal. Then the flow rate may be calculated 96, from, for example, pressure differential across a pressure reducing device, pitot tubes, or from a hot wire anemometer.

Optionally, a graphical user interface (GUI) may be provided that graphically displays the real-time flow rate of injectate 98. The display may include limits within which the flow rate should appear. The timer may be stopped 100 upon receiving a signal of a drop in the pressure at a selected one or both of the pressure sensors. Volume is calculated 102 using the flow rate and the measured elapsed time. A signal from a temperature sensor is received to indicate the temperature of the injectate 104, and the volume and temperature are used in the calculation of at least one transpulmonary thermodilution parameter 106.

Figure 4:
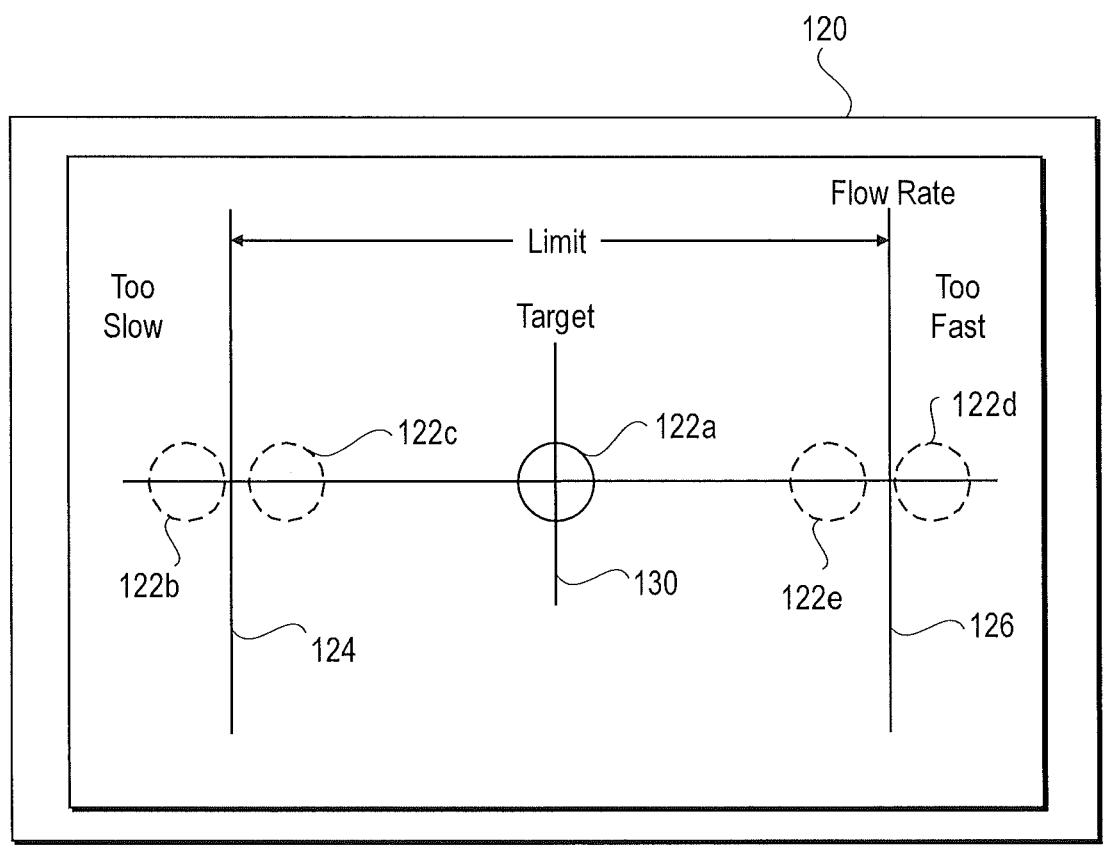
FIG. 4 is a screenshot of a screen of the display device that is part of the system of FIG. 2. Such a screen may be produced by embodiments of the invention.

FIG. 4 shows a monitor 120 associated with a computer 42 (FIGS. 1 and 2). The monitor 120 may display a GUI of the flow rate of injectate from the syringe 26 into the catheter 50. The flow rate may be displayed in real time, as represented in this embodiment by a bubble 122*a*. The flow rate increases from left to right in FIG. 3. A minimum limit 124 and a maximum limit 126 of flow rate may be displayed on the monitor 120. The target 130 may be centrally located, and various example positions of the bubble being shown in dashed lines. A second bubble 122*b* shows that the flow rate is too slow, as it is outside the acceptable range and below the minimum limit 124. A third bubble 122*c* shows that the flow rate is acceptable but should be increased, as it is just within the acceptable range and above the minimum limit 124. A fourth bubble 122*d* shows that the flow rate is too fast, as it is outside the acceptable range and above the maximum limit 126. A fifth bubble 122*e* shows that the flow rate is acceptable but should be decreased, as it is just within the acceptable range and below the maximum limit 124. The user applying force to the syringe 26 may watch the monitor 120 for direction regarding how fast the plunger of the syringe 26 should be depressed and accordingly what force should be applied to result in an acceptable flow rate.

Figure 5:
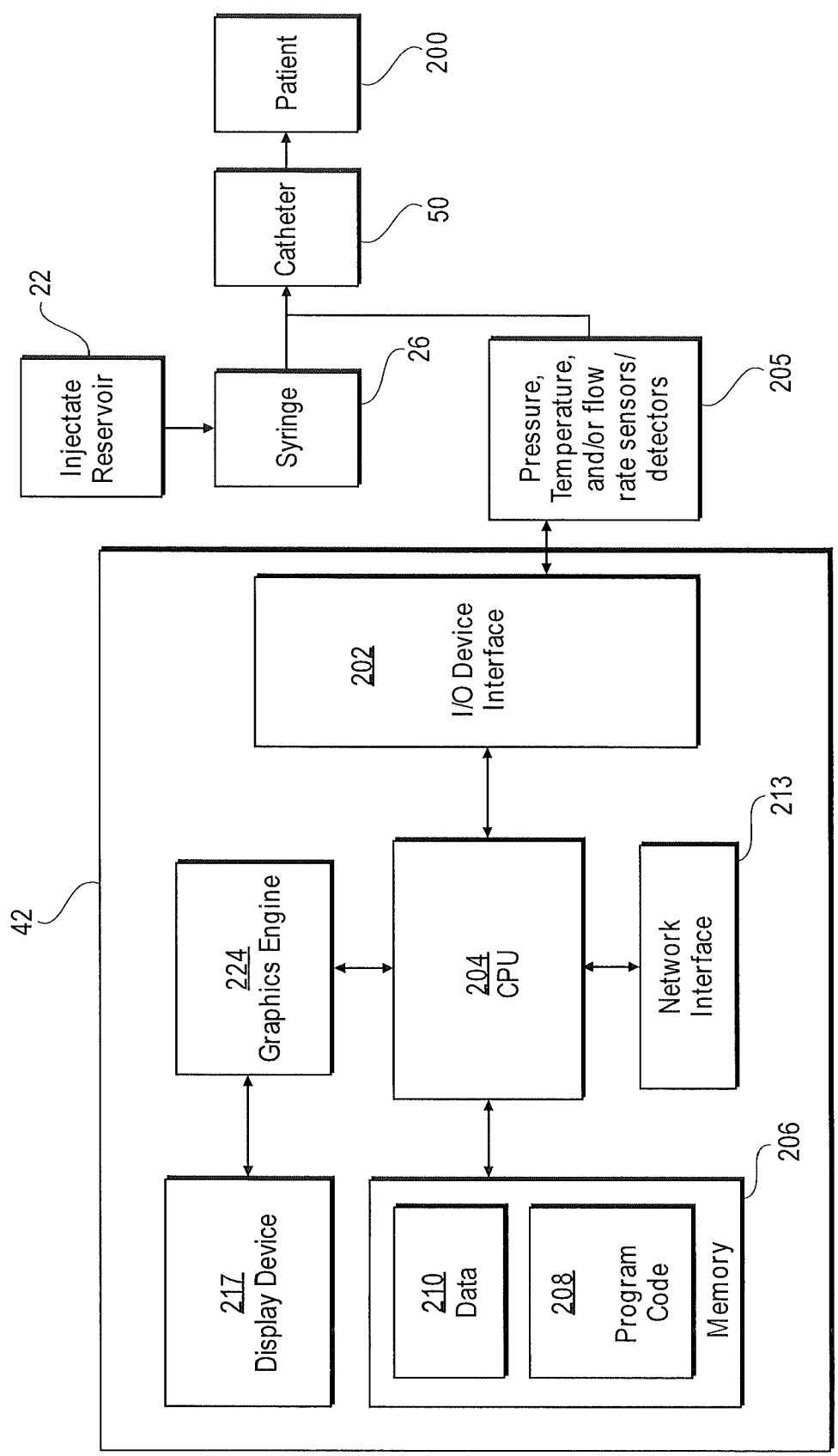
FIG. 5 is a block diagram of a system according to example embodiments of the invention.

FIG. 5 schematically illustrates detail of the computer 42 with associated CPU, monitor, and control unit of FIG. 1, also showing selected other features of an injectate delivery system as well as a patient 200. The system includes I/O interface 202, which may in turn include an appropriate connector, and circuitry to monitor signals from the sensor system. This circuitry may include analog-to-digital converters, encoders, decoders, and the like. I/O interface 202 is coupled to a central processing unit (CPU) 204, which controls the operation of the entire system.

The I/O interface receives sensor signals from pressure sensors, temperature sensors, and/or flow rate detectors 205, and the like. CPU 204 is further operatively connected to memory 206. Memory 206 stores all of the information needed for the system to operate. Such information may be stored in a temporary fashion, or may be stored more permanently. This memory may include a single, or multiple types of memory. For example, a portion of the memory connected with CPU 204 may be "flash" memory which stores information semi-permanently for use by the system. In either event memory 206 of FIG. 5 in this example embodiment includes computer program code 208 which, when executed by CPU 204, causes the system to carry out the various processes to graphically display information according to example embodiments disclosed herein. Memory 206 also stores data 210, which in example embodiments includes historical numerical values for the pressures, temperatures, times, flow rates, and injectate volumes.

Still referring to FIG. 5, monitoring and control unit 12 may also include a network interface 213. This network interface can allow the system to be connected to a wired or wireless network to allow monitoring on a remote display (not shown). For example, the remote display could duplicate, or be used in place of the local display panel. In the embodiment of FIG. 5, a local display device, 217 (which may be the same as monitor 120 of FIG. 4), is connected with CPU 204 via a graphics engine 224. The local display device may be an LCD panel, plasma panel, or any other type of display component and accompanying circuitry to interface the display device to graphics engine 224. Graphics engine 224 may be on its own chip, or in some embodiments it may be on the same chip as CPU 204. Note that display device 217 may include user input functionality, for example an optical or capacitive touchscreen over the display screen. In such a case, monitoring control unit 42 may include additional circuitry to process such input. Alternatively, such circuitry may be included in the display device itself, the graphics engine, or the CPU 204.

Figure 6:
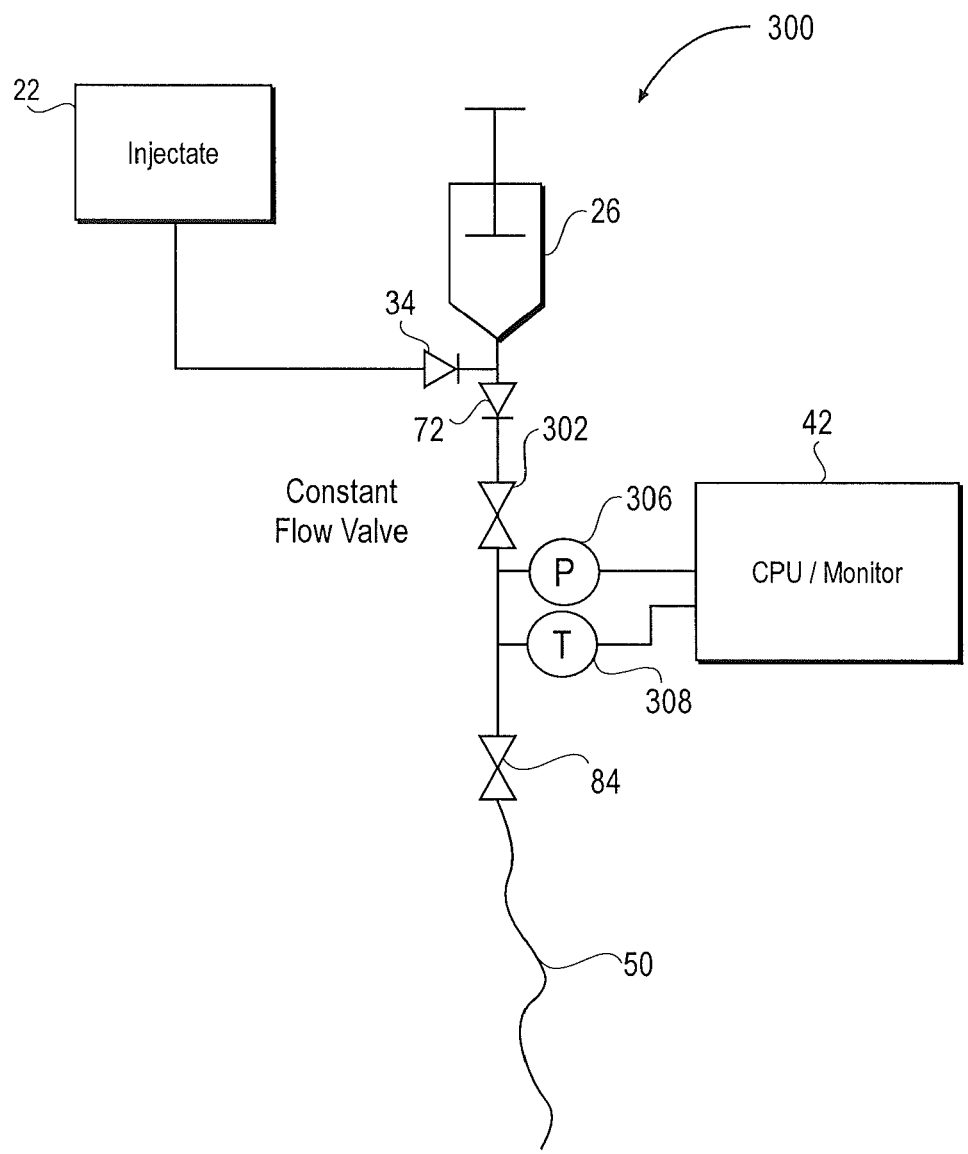
FIG. 6 is a schematic view of another injectate delivery system in accordance with example embodiments of the invention.

FIG. 6 schematically shows another example embodiment according to the invention of an injectate delivery system 300. Similarly to the injectate delivery system 70 of FIG. 2, the injectate delivery system 300 of FIG. 6 may include a reservoir such as a syringe 26 that may draw from an injectate reservoir 22, with a check valve 34 allowing flow from the reservoir 22 but preventing flow back to the reservoir 22. Alternatively, the reservoir 22, tubing 24, and check valve 34 may be omitted, leaving the system closed, with only the syringe 26 as the source of injectate; the syringe 26 may be pre-filled and itself cooled. Another check valve 72 may be provided that allows the flow of discharged injectate from the syringe 26, but prevents backflow into the syringe 26 from tubing 24 when the syringe 26 is aspirated to draw injectate from the reservoir 22. In this embodiment, however, a constant flow valve 302 may be inserted in line with the tubing 24. The constant flow valve 302 will remain closed until a "cracking pressure" is reached from actuating the plunger of the syringe 26, at which time the seal will open and flow will begin, being maintained at the same constant flow rate based on the design of the valve. The pressure required to break the seal may be on the order of, for example, one pound. Alternatively, a constant flow syringe may be provided, combining the syringe and the constant flow valve.

A pressure sensor 306, and a temperature sensor 308, which may be a thermistor, may be provided in line with and preferably downstream of the constant flow valve 302. The pressure sensor 306 and temperature sensor 308 may be connected to the computer 42 with cables 44. The pressure sensor 306 may be useful to initiate and stop the timer to allow volume calculation based on the flow rate of the valve multiplied by the elapsed time, while the temperature sensor 308 is needed for the thermodilution calculation. A stopcock 84 or other valve may be provided and may be connected to a proximal injectate hub (not shown). The catheter 50 is represented by a single line in FIG. 6, but it should be understood that there may be multiple connection lines incorporated in the catheter that serve a variety of functions, as exemplified in FIG. 1.

The materials of components of the apparatus disclosed herein may be as selected by one of ordinary skill in the medical equipment design arts.

As discussed above, the thermodilution algorithm is sensitive to the injectate volume that is applied to the patient. If the injectate volume is incorrectly input into the system, or the volume applied to the patient is different, then the computational values are not accurate. To demonstrate the influence of the injectate volume on the results of key transpulmonary thermodilution parameters, an analysis was performed. Using a thermodilution bolus from a clinical study, the output parameters using a range of injectate volumes between 10 mL to 20 mL were recalculated to allow review of the range and error of the parameter values resulting from incorrect injectate volumes. The impact of injectate volume on the three primary transpulmonary thermodilution parameters of cardiac output, global end diastolic volume, and extra vascular lung water was considered.

The procedure used a thermodilution bolus from a clinical study to recalculate the output parameters using a range of injectate volumes between 10 mL to 20 mL, then to study the range and error of the parameter values resulting from incorrect injectate volumes. The results were as follows:

| Injection Volume (mL) | CO (L/min) | GEDV (mL) | EVLW (mL) |
|---|---|---|---|
| 10 | 3.28 | 1005.7 | 304.2 |
| 11 | 3.64 | 1105.6 | 332.7 |
| 12 | 4 | 1205.4 | 316.3 |
| 13 | 4.35 | 1305.2 | 389.8 |
| 14 | 4.71 | 1405.1 | 418.4 |
| 15 | 5.07 | 1504.9 | 447 |
| 16 | 5.43 | 1604.7 | 475.5 |
| 17 | 5.79 | 1704.6 | 504.1 |
| 18 | 6.15 | 1804.4 | 532.6 |
| 19 | 6.51 | 1904.3 | 561.2 |
| 20 | 7.01 | 2004.1 | 589.7 |

Figure 7:
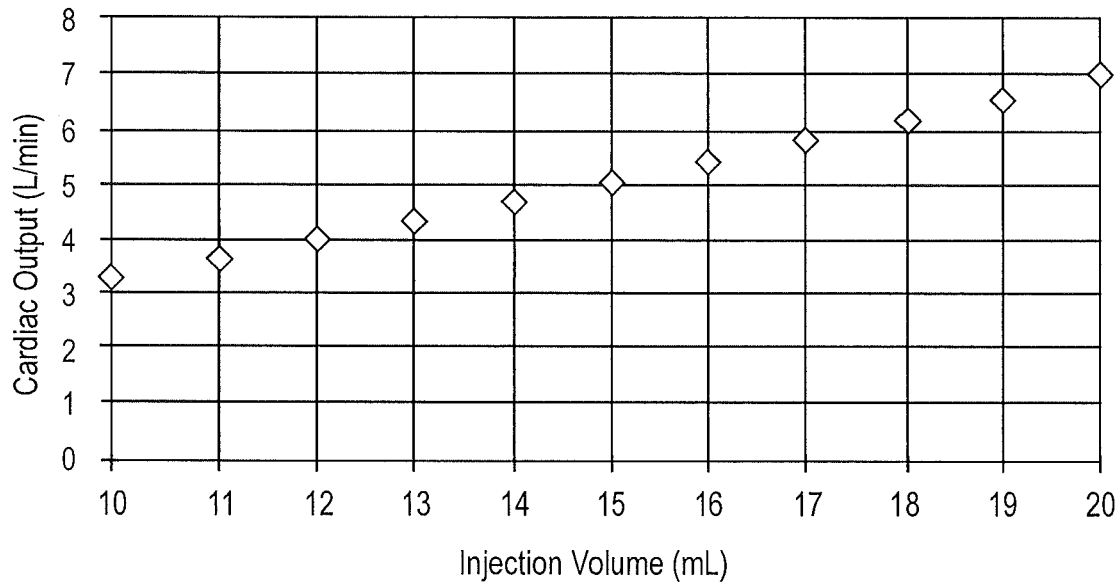
FIGS. 7-9 are graphs representing the impact of incorrect injectate volume, either being injected or recorded, on transpulmonary thermodilution parameters.
Figure 8:
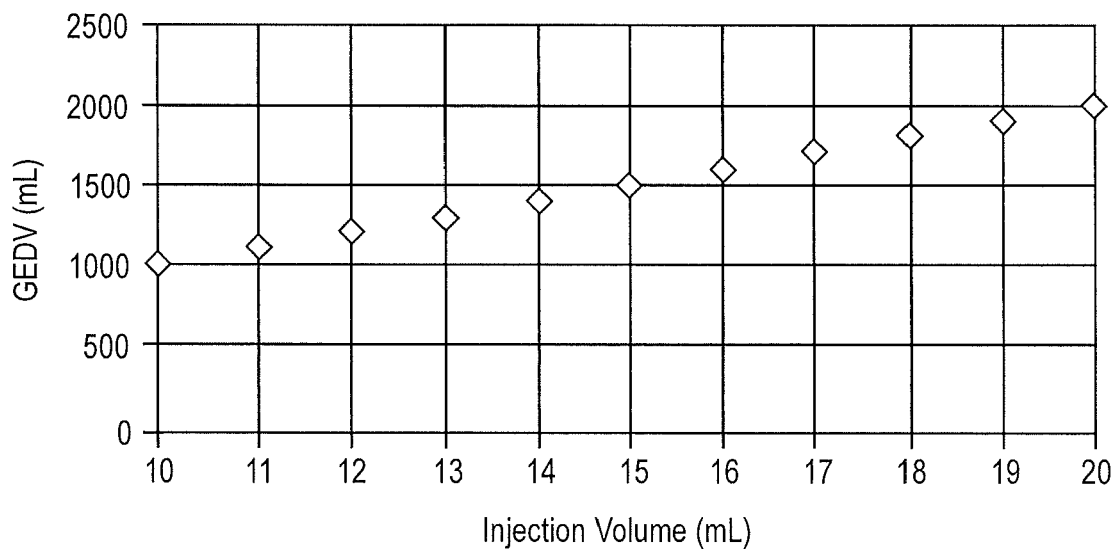
Figure 9:
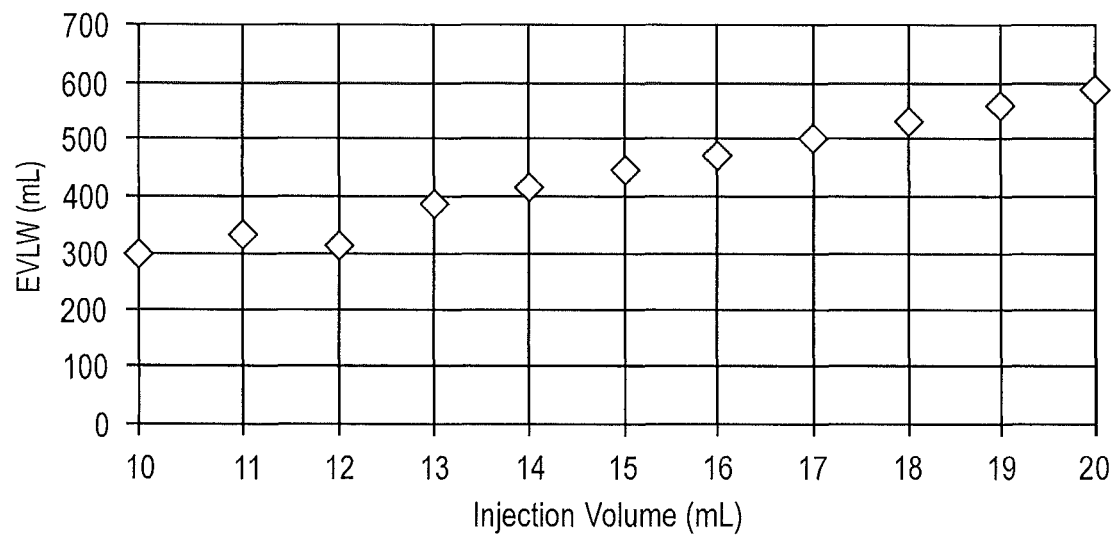

FIGS. 7-9 show the results plotted with the parameters each as a function of injectate volume. The graphs and the table above show that assuming the original 10 mL value is correct, in this particular example, if 20 mL is incorrectly injected rather than the intended 10 mL, there can be an error of up to 114% with respect to CO (FIG. 7), an error of up to 99% with respect to GEDV (FIG. 8), and an error of up to 94% with respect to EVLW (FIG. 9).

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure. The following claims are in no way intended to limit the scope of the disclosure to the specific embodiments described herein. While the foregoing is directed to embodiments of thermodilution injectate measurement and control, other and further embodiments may be devised without departing from the basic scope thereof, and the scope thereof is determined by the claims that follow.

What is claimed is:

1. An injectate delivery system, comprising:
a reservoir for holding a fluid injectate;
a conduit in fluid communication with the reservoir and configured at one end to be connected to a catheter, the conduit comprising an elongate tubing configured to receive discharged injectate from the reservoir;
an injector configured to discharge the fluid injectate from the reservoir to the conduit;
a flow measurement device interposed in the conduit between the reservoir and the catheter and within the elongate tubing, wherein the flow measurement device is configured to generate a signal; and
a processing device adapted to receive the signal from the flow measurement device and configured to calculate:
flow rate of the fluid injectate from the reservoir to the catheter based at least in part on the signal; and
injectate volume, based at least in part on the calculated flow rate, to be used as input for calculating at least one parameter.

2. The system of claim 1, wherein the at least one parameter is cardiac output.

3. The system of claim 1, wherein the reservoir is a reservoir of a syringe that includes a manually operable plunger as the injector.

4. The system of claim 3, wherein the catheter is in fluid communication with the reservoir.

5. The system of claim 4, wherein the catheter is a Swan-Ganz catheter.

6. The system of claim 1, wherein the flow measurement device is configured to generate the signal based on differential pressure.

7. The system of claim 1, further comprising:
a first pressure sensor situated upstream of the flow measurement device and in line with the elongate tubing; and
a second pressure sensor situated downstream of the flow measurement device and in line with the elongate tubing;
wherein the first and second pressure sensors are configured to measure a pressure drop across the flow measurement device.

8. The system of claim 1, further comprising:
a first pressure sensor situated upstream of the flow measurement device and in line with the elongate tubing; and
a second pressure sensor situated downstream of the flow measurement device and in line with the elongate tubing;
wherein:
the first and second pressure sensors are configured to measure vortex differential pressure, and
the flow measurement device defines an area of constricted flow.

9. The system of claim 1, wherein the flow measurement device comprises a Venturi tube.

10. The system of claim 1, wherein the flow measurement device comprises one or more pitot tubes.

11. The system of claim 1, wherein the flow measurement device comprises a hot wire anemometer.

12. The system of claim 1, further comprising a sensor interposed in the conduit downstream of the flow measurement device, wherein the sensor is configured to detect changes in pressure or temperature of the fluid injectate and to signal a timer to start at a beginning of an injection of the injectate and stop at an end of the injection to measure elapsed time of the injection.

13. The system of claim 1, wherein the processing device is further configured to display the calculated flow rate of the fluid injectate in real time.

14. The system of claim 1, further comprising a valve for allowing discharge from the reservoir, wherein the flow measurement device is situated downstream of the valve.

15. The system of claim 1, wherein the flow measurement device is not situated within the reservoir or the injector.

16. The system of claim 1, wherein the flow measurement device is entirely within the elongate tubing.

17. An injectate delivery system, comprising:
a reservoir for holding a fluid injectate;
a conduit in fluid communication with the reservoir and configured at one end to be connected to a catheter;
an injector configured to discharge the fluid injectate from the reservoir to the conduit;

a first pressure sensor connected in line with the conduit, wherein the first pressure sensor is configured to generate a first signal;
a second pressure sensor connected in line with the conduit;
a flow measurement device interposed in the conduit downstream of a first connection point between the first pressure sensor and the conduit and upstream of a second connection point between the second pressure sensor and the conduit, the flow measurement device comprising:
 a pressure reducing feature; and
 configured to generate a third signal;
wherein:
 the first pressure sensor is further configured to generate the first signal in response to detecting an increase in pressure;
 the first pressure sensor or the second pressure sensor is configured to generate a second signal in response to detecting a decrease in pressure; and
 the processing device is further configured to:
  start a timer upon receiving the first signal;
  receive the second signal;
  stop the timer upon receiving the second signal;
  receive the third signal;
  calculate flow rate of the injectate based at least in part on the third signal;
  determine cardiac output based at least in part on:
   an elapsed time between the first signal and the second signal; and
   the calculated flow rate.

18. The injectate delivery system of claim 17, further comprising:
 a constant flow valve in line with the conduit and configured to maintain a constant flow rate at the conduit; and
 a temperature sensor configured to generate a fourth signal;
 wherein the processing device is further configured to determine cardiac output based at least in part on the first signal, the fourth signal, and the constant flow rate.

19. The injectate delivery system of claim 17, further comprising:
 a constant flow valve in line with the conduit and configured to maintain a constant flow rate at the conduit, wherein:
 the first pressure sensor is further configured to generate the second signal in response to detecting the decrease in pressure; and
 the processing device is further configured to:
 start the timer upon receiving the first signal;
 receive the second signal;
 stop the timer upon receiving the second signal; and
 calculate volume of the injectate based at least in part on the constant flow rate and an elapsed time between the first signal and the second signal.

* * * * *